(12) United States Patent
Håkansson

(10) Patent No.: US 6,840,919 B1
(45) Date of Patent: Jan. 11, 2005

(54) PERCUTANEOUS BONE ANCHORED TRANSFERRING DEVICE

(75) Inventor: Bo Håkansson, Göteborg (SE)

(73) Assignee: Osseofon AB, Gothenburg (SE)

( * ) Notice: Subject to any disclaimer, the term of this patent is extended or adjusted under 35 U.S.C. 154(b) by 0 days.

(21) Appl. No.: 09/581,058

(22) PCT Filed: Dec. 17, 1998

(86) PCT No.: PCT/SE98/02367
§ 371 (c)(1),
(2), (4) Date: Jul. 24, 2000

(87) PCT Pub. No.: WO99/34754
PCT Pub. Date: Jul. 15, 1999

(30) Foreign Application Priority Data

Dec. 18, 1997 (SE) ............................................... 9704752

(51) Int. Cl.⁷ ......................... A61M 5/32; A61M 31/00; A61F 2/02; H01R 13/60; A61B 5/05
(52) U.S. Cl. .................... 604/175; 604/197; 604/93.01; 623/11.11; 439/39; 600/345
(58) Field of Search .................... 604/288.01–288.04, 604/174–175, 523, 533–539, 93.01, 197, 104, 228.02, 246; 607/115–118, 126; 606/69–71, 151; 285/96; 600/345, 573, 576, 584, 375; 439/39, 374, 923, 180, 21; 29/825; 264/263

(56) References Cited

U.S. PATENT DOCUMENTS

| | | | |
|---|---|---|---|
| 3,870,832 A | | 3/1975 | Fredrickson |
| 3,995,644 A | | 12/1976 | Parsons |
| 4,025,964 A | | 5/1977 | Owens |
| 4,328,813 A | * | 5/1982 | Ray ........................... 607/139 |
| 4,495,917 A | | 1/1985 | Byers |
| 4,629,451 A | | 12/1986 | Winters et al. |
| 4,874,316 A | * | 10/1989 | Kamon et al. ................. 439/39 |
| 5,507,303 A | * | 4/1996 | Kuzma ....................... 128/899 |
| 5,562,670 A | * | 10/1996 | Brangnemark ............... 606/73 |
| 5,604,976 A | | 2/1997 | Stobie et al. |
| 6,080,134 A | * | 6/2000 | Lotti et al. ................... 604/175 |
| 6,473,654 B1 | * | 10/2002 | Chinn ........................ 607/126 |

FOREIGN PATENT DOCUMENTS

| | | |
|---|---|---|
| SE | C2 503 790 | 9/1996 |
| WO | WO 97/13477 | 4/1997 |

* cited by examiner

Primary Examiner—Nicholas D. Lucchesi
Assistant Examiner—Roz Maiorino
(74) Attorney, Agent, or Firm—Oppedahl & Larson LLP

(57) ABSTRACT

The present invention relates to a percutaneous bone anchored transferring device and a connecting device for obtaining a transfer of an electrical signal and/or energy and/or distribution of a drug and/or airing of a body cavity and a system and a method for using the same.

12 Claims, 13 Drawing Sheets

PERCUTANEOUS BONE ANCHORED TRANSFERRING DEVICE

CROSS-REFERENCE TO RELATED APPLICATIONS

This application is a §371 national phase of International Application No. PCT/SE98/02367 filed on Dec. 17, 1998.

BACKGROUND OF THE INVENTION

The present invention relates to a percutaneous (skin penetrating) bone anchored transferring device and a connecting means, preferably by means of which an outer device can be connected to an inner implanted subcutaneous unit.

In spite of an increasing need for a percutaneous connecting device for permanent use, in particular for the transfer of electrical information and/or electric energy there is no commercially available unit being allowed for clinical use in spite of the fact that there are several patents within the field. It is believed that the reason that these patents have so far not led to any commercial product is probably due to the fact that the patents describe connecting devices which are either too complicated in that they contain too many poles and ingoing components or that they do not attend to all the intricate demands raised from biocompatibility, anatomical, surgical, electrical, patient safety and handling points of view. Some of the published patents in this field are described below.

In U.S. Pat. No. 5,562,670 to Brånemark an electrical connecting device is described which is applied by means of a threaded tubular implant where its inwardly turned end has a central bore. The contact means and the set of cables are introduced and fixed from the outside of the implant. This is a patent by the pioneer and the inventor of titan implants of today concerning dental rehabilitation, bone anchored hearing aids, and face prosthesis, knee and finger joints, etc. When it comes to practical realization of the electric connecting device described in U.S. Pat. No. 5,562,670 there is a weakness in that the implanted set of cables and the inner implanted unit have to be so small that they can pass through the central bore of the implant. For most applications, however, the inner implant is too large to be able to pass through the central bore of the implant. In these cases the units have to be surgically implanted as an integrated unit or become mounted together with the implant in place or become connected by means of a second implanted connecting device that is small enough. If the contact means should be repaired or maintained, which is necessary with regard to the environment that a skin penetrating implant is subject to (contact surfaces become oxidized etc.), this has to be done in the skin penetrating abutment itself. If one should wish to remove/exchange the connecting device the whole implanted set of cables has to be removed. Fixation of the implant using threads has the disadvantage that the bone anchored part of the implant has to have a diameter large enough to encompass the thread, which clearly restricts the possibilities to encompass connecting components therein as well. It is desirable to be able to encompass the connecting components in the bone anchored part of the transferring device to reduce the total height of the transferring device. A well functioning transferring device should not extend outside the skin level more than 1 to 3 mm in order to avoid damages from possible outer mechanical violence and in order that the implant should be experienced as acceptable from an aesthetical point of view. Furthermore, a screw implant has to be rotated during the application which means that an asymmetrical design of the implant is very hard to realize. An asymmetrical design of the implant is desirable as the bone thickness where the implant has to be placed is so thin that the set of cables has to leave the implant in a radial direction. Furthermore, practical problems will result because the inner implanted unit has to rotate together during application if it has been pre-mounted and passes through the transferring device due to the fact that it is too large to be applied afterwards through the bore.

U.S. Pat. No. 3,870,832 to Fredricson discloses a connecting device for the application of a microphone, which device corresponds, in principle, with the Brånemark patent. Fredricson shows that the retention of the microphone element is done using a locking nut which is applied using an outwardly turned thread on the implant. Such design would lead to a potential risk for bacterial accumulation and risk for skin irritation. Additionally, the design according to this patent, is subject to the same weaknesses as described above with reference to patent U.S. Pat. No. 5,562,670.

U.S. Pat. No. 5,604,976 to Stobie et al discloses a connecting device for a great number of conductors, the inner part of which is not intended to be lowered beneath the outer limiting surface of the bone, but instead becomes fixed above the same but below the soft tissue. In this connecting device the set of cables lead to the inner implanted unit on the top of the bone but beneath the soft tissue. Problems reported in clinical tests using such an arrangement shows that the set of cables having a realistic minimum diameter of 1 to 2 mm and being a little elastic creates a biocompatibility problem at the skin penetration area, probably due to the occurrence of small movements between the mobile skin and bone with a foreign material there between. Furthermore, the necessary skin reduction can be jeopardized if the set of cables does not have a very small diameter. The connection can be severed apart by means of tools to loosen a screw connection, but can not, for any reason, be disconnected in daily use. This connecting technique further means that rotation of the outer connecting part is not possible and that the device is not protected from excessive external forces.

U.S. Pat. No. 5,507,303 to Kuzma discloses a connecting device where the implant is anchored to the scull bone but where the skin/bone connecting tissue closest to the implant is separated from the scull bone using a large flange. Experience from skin penetrating titan implants in the scull bone shows that it is of utmost importance that the skin around the penetration area has been adequately reduced in thickness and that the thickness reduced skin is allowed to grow against bone connecting tissue and scull bone (Tjellstrom, Anders, et al, The Bone Anchored Hearing Aid—design principles, indications and long-term clinical results, Otolaryngologic Clinics of North America, vol 28(1), 1995, pp 53–72). The flange of the actual connecting device hinders the skin from growing to the bone/bone connecting tissue, and the frequency of skin complications can be expected to be relatively high. Furthermore, the whole connecting device is placed outside both the bone and the skin, which means that it will extend a considerable distance above the skin surface. The retention between the connecting parts is done using magnetic force.

U.S. Pat. No. 4,025,964 to Owens discloses a connecting device which unlike the connecting devices above is not anchored to the bone in a stable way. Even small movements of the implant relative to the skin will lead to a great risk for skin irritation. Fixation between the male and female parts of the connecting device is carried out using magnetic attraction force and the parts can not be rotated relative to each other.

U.S. Pat. No. 3,995,644 to Parsons discloses a connecting device as well, which is merely fixed to the skin and intended to transfer an electrical signal, preferably for electrical stimulation of muscle units. Due to the fact that even small movements between skin and implant create irritation, this type of connecting devices should only be used temporarily.

U.S. Pat. No. 4,328,813 relates to a system for anchoring a brain cable and is only intended to geometrically fix or lock a cable such as an electrode for the stimulation of a certain point in the brain. The cable is thereby intended to be brought underneath the scalp to an electric stimulator. As the implant is manufactured in an elastic material, which is provided with slots, the implant can not be used for a bone anchored percutaneous transferring device.

SE-C-503,790 relates to a passive screw implant for the transfer of vibrations from an outer vibrator (loud speaker) to the scull bone. Such an implant can not transfer electrical signals, energy or drugs to the inner body.

Finally, there are a number of connecting devices which are intended to be used totally subcutaneously, such as U.S. Pat. No. 4,495,917 to Byers, but these are so different to the present invention concerning functional requirements and constructive solutions that a further analysis does not seem to be meaningful.

An improved connection/transferring device that is designed for daily use, such that the connection is simple and allows substantially free rotational positioning and that the connection is easily maintained and worn out parts can be simply exchanged, is needed. Furthermore, a connection design is needed that will disconnect if subjected to a large enough outer mechanical force.

BRIEF SUMMARY OF THE INVENTION

The present invention provides a bone-anchored and skin penetrating transferring device and a connecting device designed for daily use. The connecting device comprises a first connection unit, positioned beneath the outer surface of the bone, which transfers electrical information and/or energy, drugs, etc., to an inner implanted unit. The connecting device facilitates the surgical procedure and makes it feasible to replace the inner implanted unit independent of the percutaneous bone anchored transferring device. Furthermore, the new transferring device is designed in such a way that the dimensions are small and achieve better biocompatibility.

DETAILED DESCRIPTION OF THE INVENTION

Figure 13:
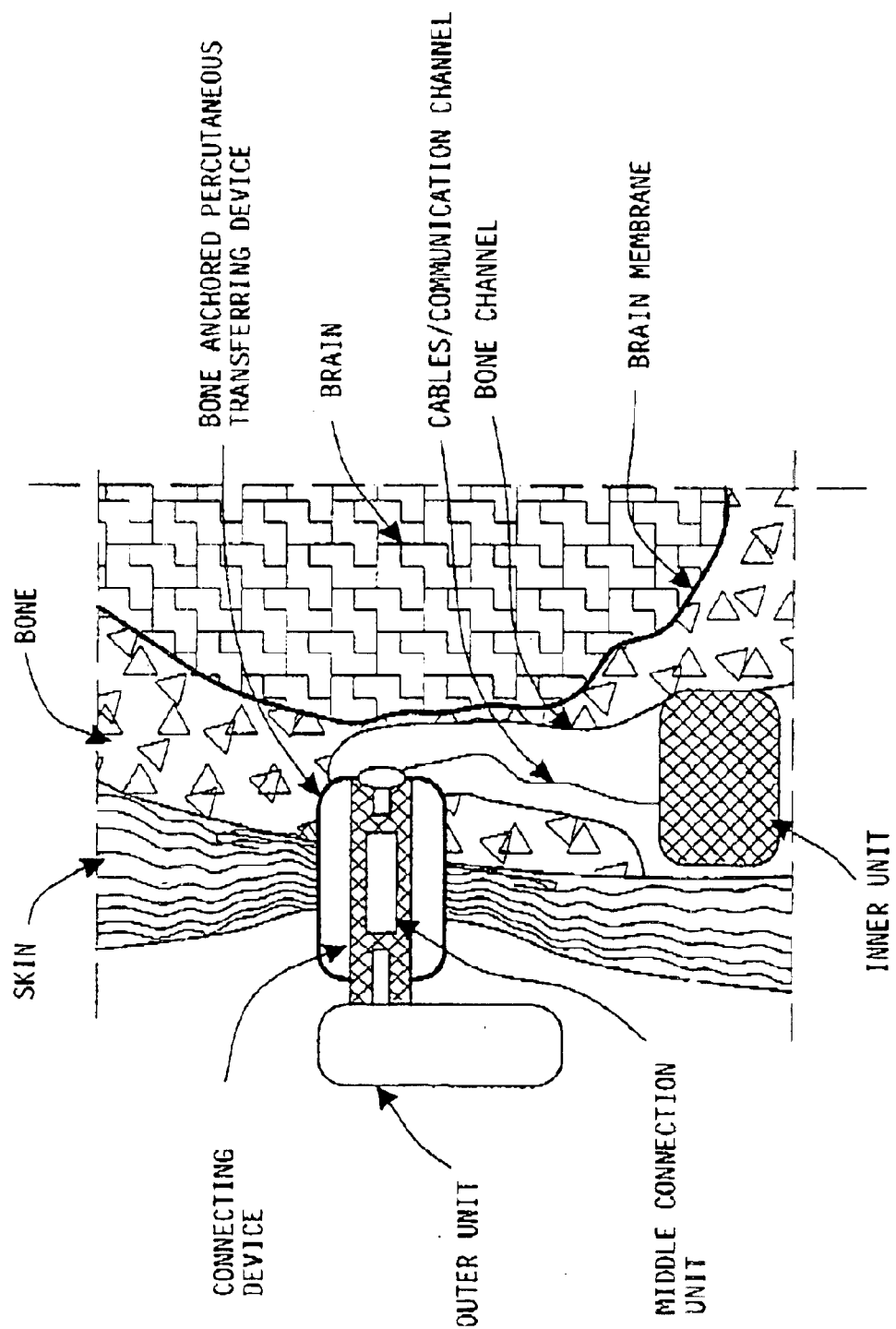
FIG. 13 shows a schematic picture of a medical-technical helping aid where a percutaneous bone-anchored transferring device according to the present invention is brought into place.

As mentioned above there is a great demand within several medical-technical applications for a means to transfer electrical information and/or electric energy or to communicate in another way (e.g. to distribute drugs or to air out interior cavities and cell systems) from an outer unit to a subcutaneously implanted inner unit. Such subcutaneously implanted units can be hearing assistive aids, e.g. cochlear implants, middle ear implants, bone conduction devices, devices for suppression of tinnitus, and other medical-technical aids, e.g. tubes, cannulas, stimulators of different types, registration means for biological signals, pumps for distribution of drugs, evacuation of liquids, etc. In principle, such devices consist of the following essential parts: outer unit, connecting device, skin penetrating and bone anchored transferring device, set of cables/communication channel, and subcutaneously implanted inner unit. A principal arrangement utilizing a transferring device according to the present invention is provided in FIG. 13, where, for example, the outer unit can be a hearing apparatus without loud speaker, and the inner unit can be a vibrator for the generation of bone conducted sound. The reason that a set of cables/communication channel between the transferring device and the inner implanted unit is needed is that the bone thickness where the transferring device from a practical and anatomical point of view has to be placed, is so thin that the inner unit will get no space. On the other hand there is plenty of space a short distance away, and closer to the auditory canal in the part of the temporal bone called the mastoid process. Where and how the inner unit will be placed is dependent upon the application.

Although the present invention can be used for other applications requiring permanent long term stable communication through the skin, the following describes an exemplary application where an outer unit can be connected electrically to an inner implanted subcutaneous unit by means of the presently proposed connecting and transferring devices. Varieties of such connecting and transferring devices are not unknown but the present invention is unique for the following reasons:

1. The application/fixation between the bone anchored skin penetrating transferring device and the set of cables takes place below the outer bone level, preferably in the bottom part of the transferring device.

The advantages using this solution are a. that the set of cables and the implanted inner unit each can be assembled and disassembled separately, which is not only essential for facilitating the surgical installation but in particular at future events, such as skin irritation/damages/maintenance/updates when the bone anchored and skin penetrating transferring device and the set of cables (optionally including the inner unit), respectively, need to be exchanged, most often independent from each other. Further the transferring device can be removed in such a way that intact skin can be replaced without influencing the set of cables and an inner, implanted unit. In this way all inner vital parts can be retained resting underneath the skin, simultaneously as the skin above the penetration area is replaced for a longer or shorter term period. This can be of great importance, if the patient should like to temporarily cease the treatment but have the possibility to easily resume the treatment when or if the need reoccurs;

b. that the transferring device and the set of cables (including the inner units connected to the other end thereof) can be rotated independently from each other at the surgical installation and optional dismounting, respectively.

c. that the skin closest to the penetration area can be reduced to the thickness desired, and be allowed to rest/heal to bone tissue and bone connective tissue which facilitates by the fact that the set of cables is drawn beneath and not over the outer bone surface.

2. The transferring device which is lowered into the bone tissue will have a reinforced anchoring by means of radial arms placed outside the outer surface of the bone, and will in turn be firmly screwed to the bone tissue.

The advantages using this solution are:

that a first connection unit can be placed within the bone anchoring part of the transferring device (beneath the outer bone surface) without its outer diameter becoming undesirably large. By placing part of the connecting device into the bone anchoring part of the transferring device, the part of the transferring device extending outside the skin can become minimal, which is advantageous partly from an aesthetical point of view and partly with regard to the risk for outer mechanical damage of the implant;

3. The connecting device comprises one middle connecting unit placed in the outer part of the transferring device. Two connecting devices occur; one outer to be connected to an outer unit, and one inner to be connected to the set of cables.

This solution provides the following advantages:

a. the middle connecting unit which will be exposed to the outer environment is a disposable detail designed to be simple to exchange if there should be poor electrical contact due to the appearance of an oxide layer etc, or if damage should occur in another way;

b. the middle connecting unit, in combination with a tightening ring, protects the inner and more sensitive connecting device from any outer environmental influence. Furthermore, the middle connecting unit will serve, in combination with the tightening ring, as a first biological barrier against the passage of undesired compounds/bacteria to the tissue inside the transferring device. The main barrier in this respect, is, however, the screw joint between the connecting means of the transferring device and the set of cables;

c. the outer connecting device can be designed in such a way that it will allow free rotational positioning, will provide for a simple connection/disconnection, and will serve as an overload protection of the transferring device.

Experiences from more than 20 years of developing work with bone anchored hearing aids (Håkansson, Bo et al, The Bone Anchored Hearing Aid, Edited by Dan Tolman & P-I Brånemark, to be published) where more than 5000 patients have been operated and been provided with a mechanical bayonet coupling (SE-C-8107161-5) show that all aspects mentioned above are of importance to have a bone anchored percutaneous transferring device work in clinical use for long time. It might seem that there is a restriction in that the present invention for space reasons can hardly be realized using more than 4 to 6 poles, maintaining reasonable dimensions. If a larger number of poles is desired, as for example using the cochlear implant, wherein up to 20 to 30 electrodes is used transmission to each electrical can be accomplished using so called multiplexing. Multiplexing means that the information is transferred sequentially in a signal cable through the percutaneous electrical connection in order to then in an electronic way, become split up in the inner implanted unit and become distributed to the number of electrodes desired. Multiplexing is a well known technique when it is used within all communication (telecommunication and television) where one normally has not admittance to a single channel. That which further speaks against a great number of poles in percutaneous electrical contact is that complexity and restrictions of both medical and technical character increases dramatically using an increasing number of poles. Generally, in most applications one can manage using three poles which then might be plus, and minus poles, respectively, as well as one signal cable. In specific hearing applications one sometimes wish to drive a push-pull vibrator where two cables are signal lines and one line is the voltage supply.

Figure 1:
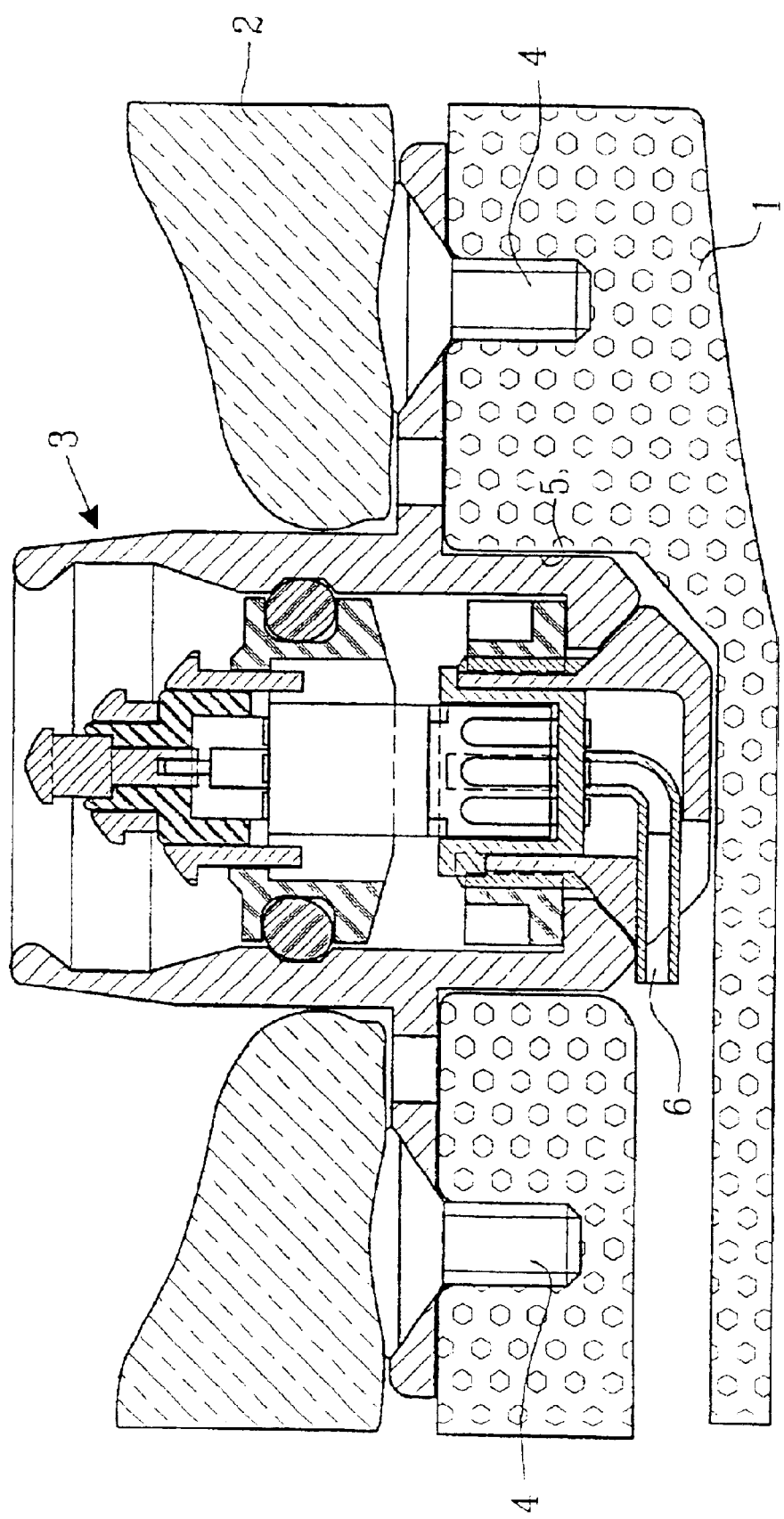
FIG. 1 is a cross sectional view of a helping aid where percutaneous bone-anchored transferring device of the present invention is utilized.

In FIG. 1, 1 denotes a skull bone with its skin and soft tissue 2, which has been thinned using known surgical technology. A percutaneous bone anchored transferring device 3 manufactured in a tissue compatible material such as titan, is anchored into the skull bone 1 using screws 4, suitable of the same type of material, attached in said bone, whereby the first connection unit is placed in the bone itself by means of a boring and lowering into the drilled hole 5. From the bottom part of the first connection unit a set of cables 6 has been drawn to an inner unit, not shown, such as a vibrator acting against the hearing bones.

Figure 2:
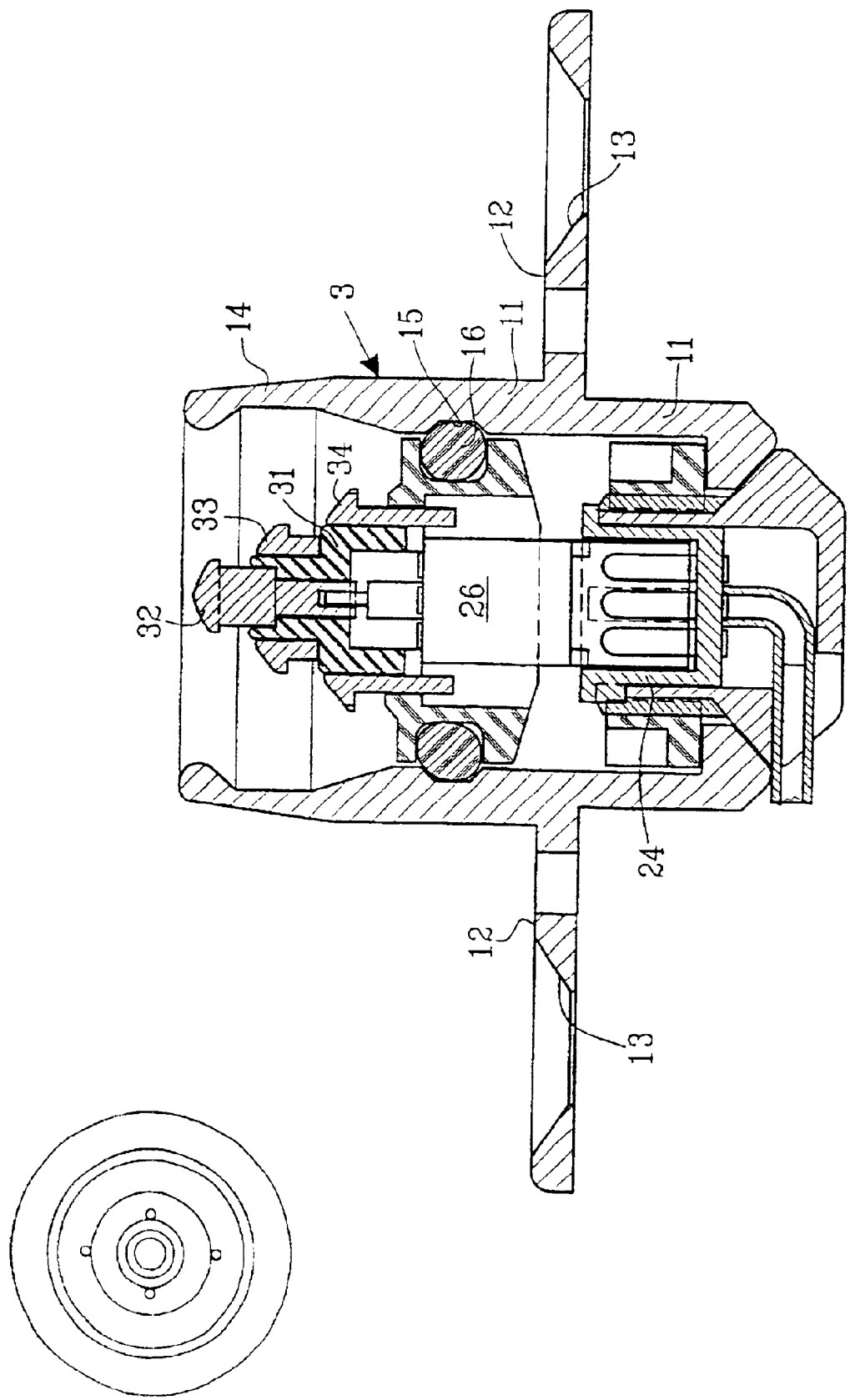
FIG. 2 is a cross sectional view of the percutaneous bone-anchored transferring device and the connecting device of the present invention.
Figure 3:
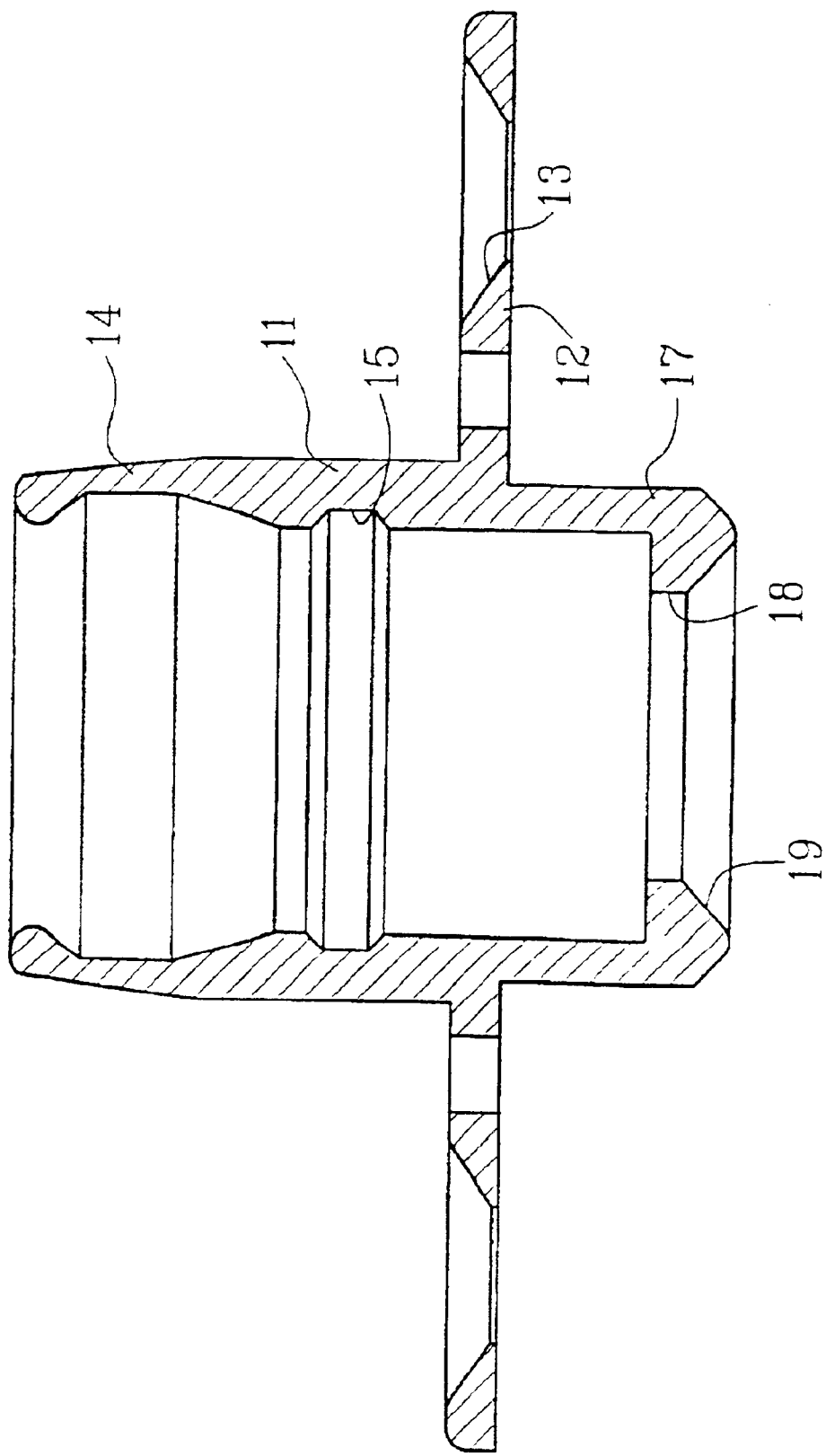
FIG. 3 shows a cross sectional view of the percutaneous bone-anchored transferring device shown in FIG. 2.
Figure 4:
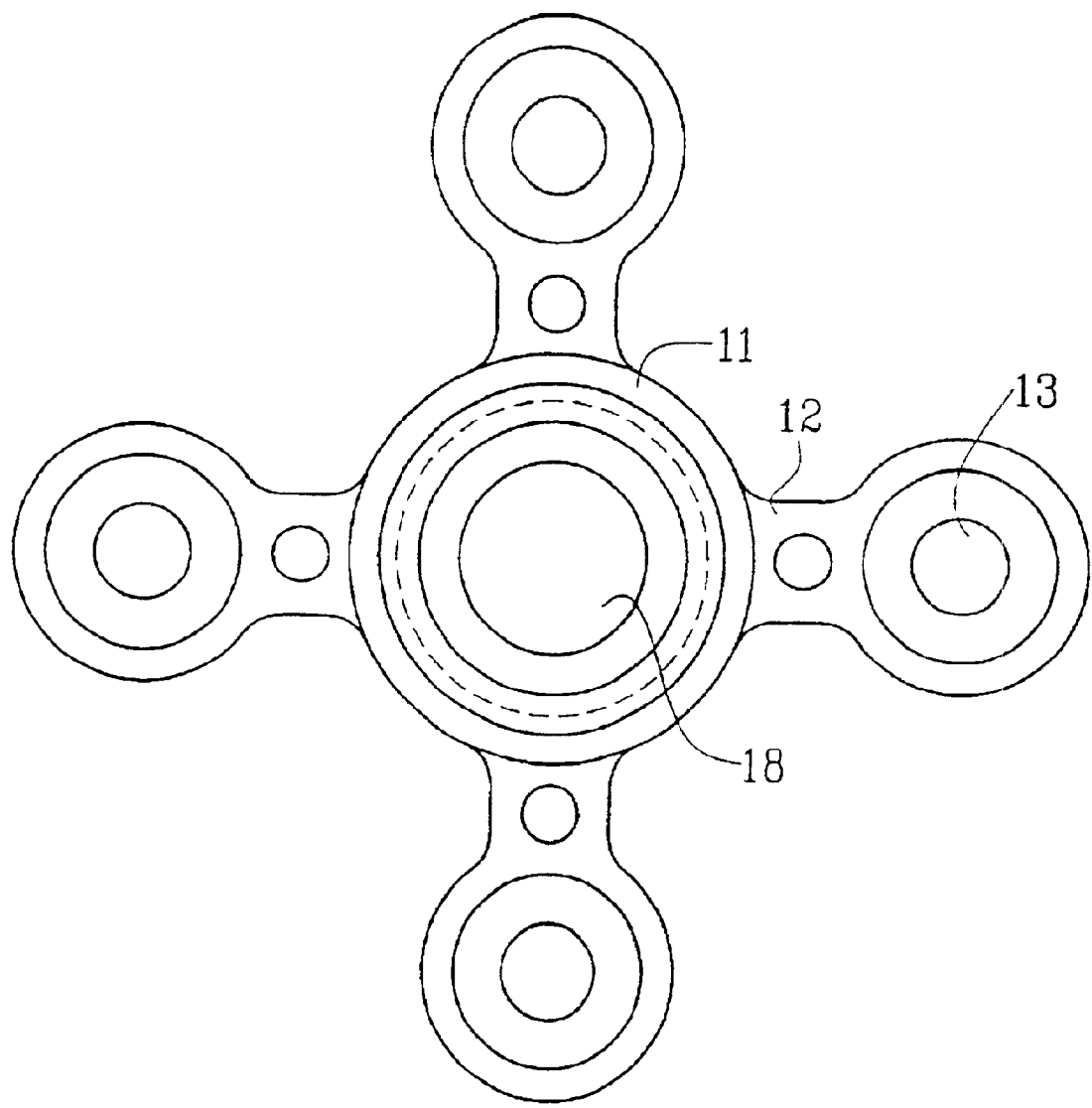
FIG. 4 shows the embodiment of FIG. 3 as seen from above.
Figure 5:
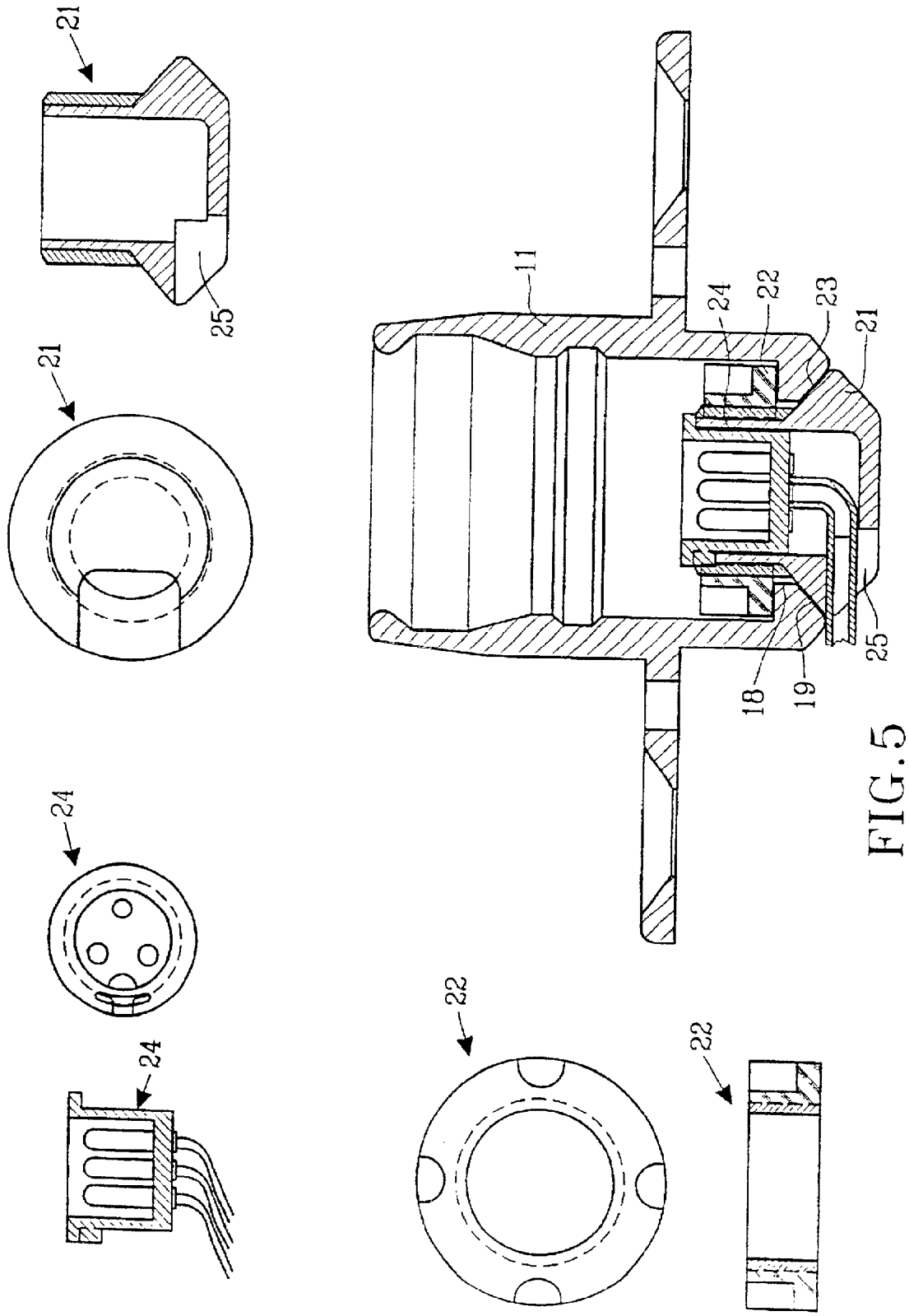
FIG. 5 shows the percutaneous bone-anchored transferring device according to FIG. 2 to 4 with the first connection unit and electrical connection unit in place.
Figure 6:
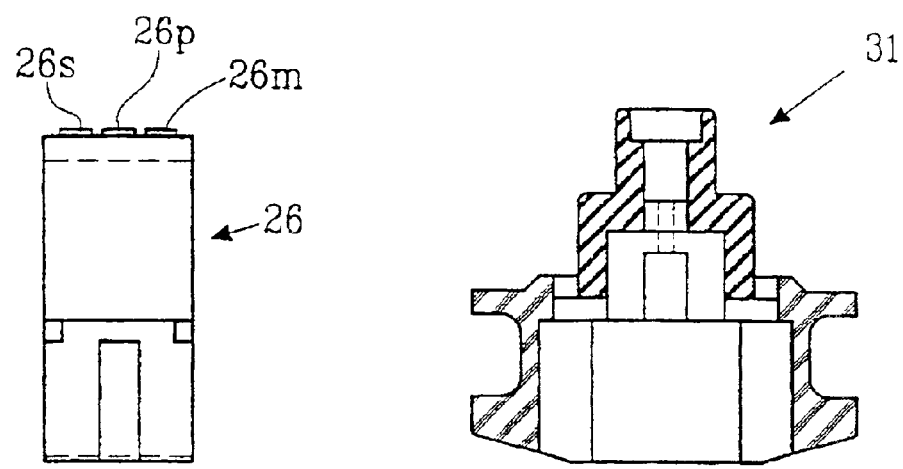
FIG. 6 shows different details of an embodiment of a middle connecting unit.
Figure 6:
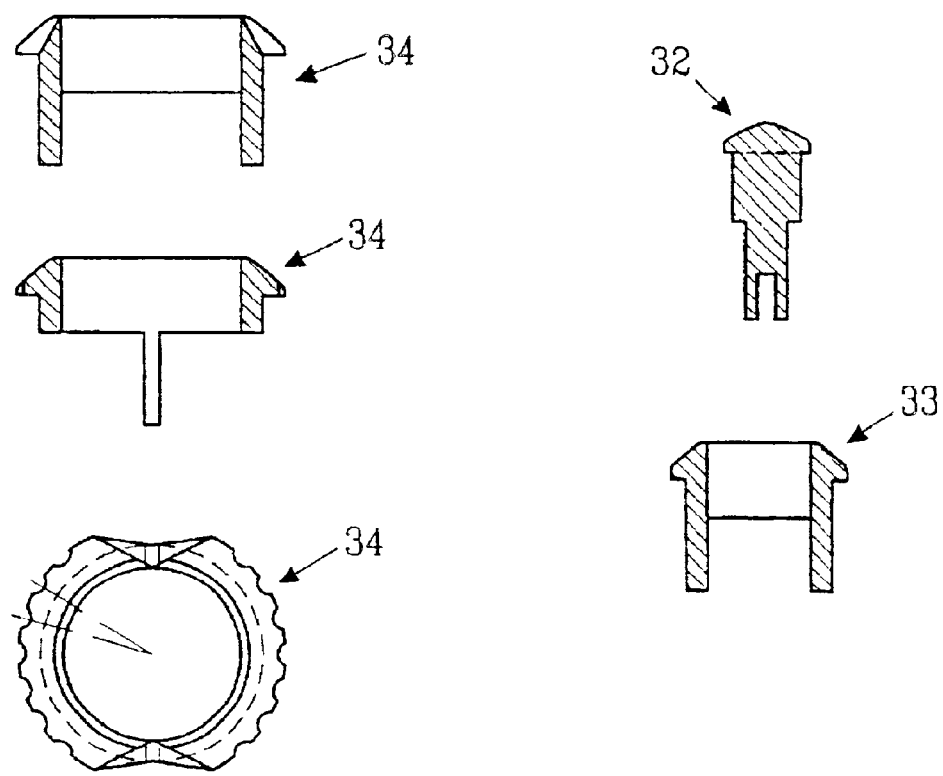
Figure 7:
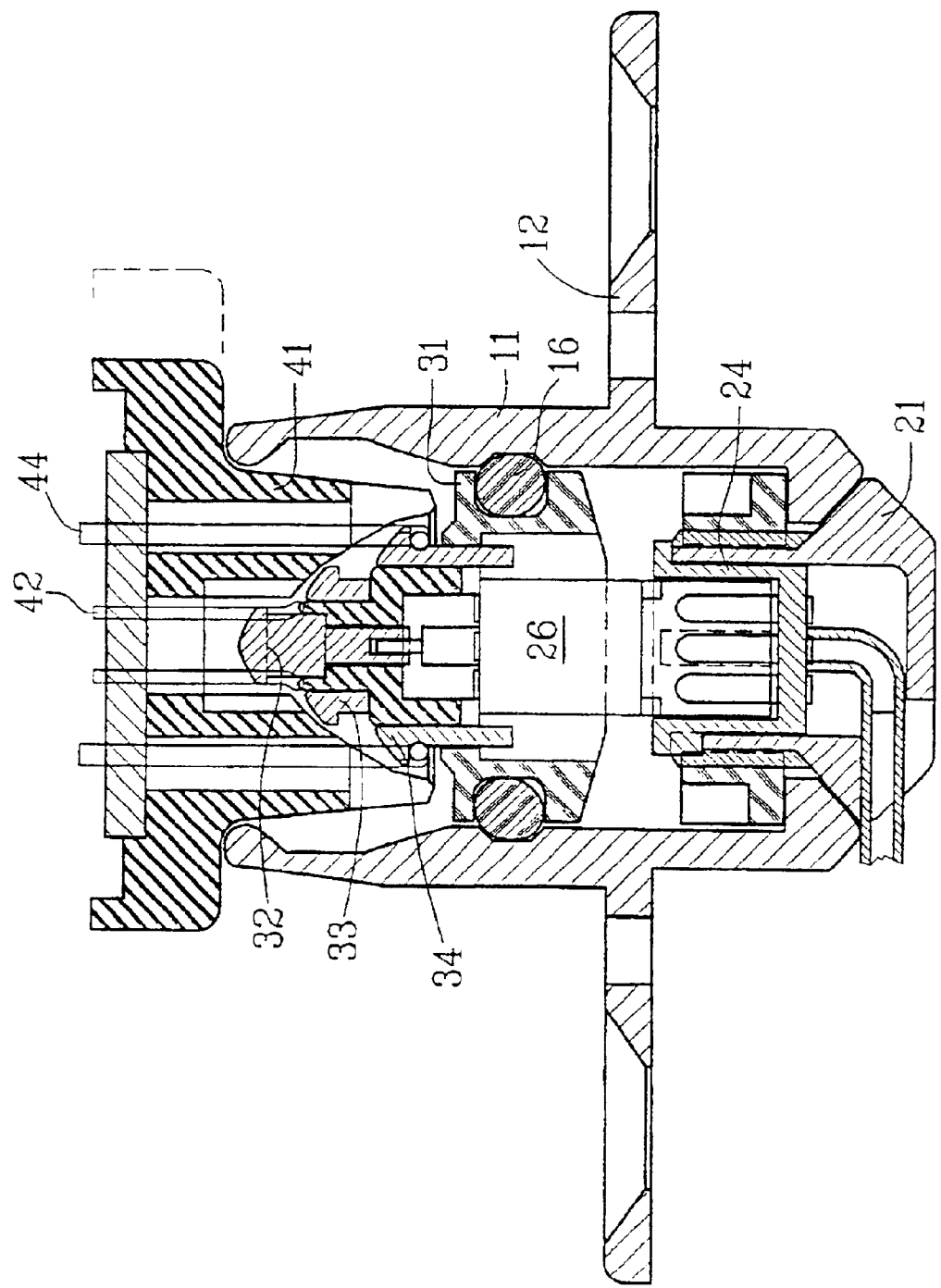
FIG. 7 shows an embodiment of the percutaneous bone-anchored transferring device and the connecting device of the present invention.

The percutaneous bone anchored transferring device 3 comprises according to FIGS. 2–4 an annular body member 11 and a number of arms 12 provided with holes 13 for carrying a screw for anchoring it by means of screws 4. The number of arms can be three, four, five or more depending on the size and intended placing. The arms 12 are pivotable and inclinable to admit maximum of adaptation to the substrate (bone, in this case) to which they shall be screwed. The percutaneous bone anchored transferring device 3 has outwardly a substantially cylindrical form with the exception of the arms 12 as well as an inwardly substantially cylindrical form. The annular body member comprises a bottom part 17, an upper part 14, a cavity, an interior surface, and an exterior surface. The cavity extends from the upper part to the bottom part. The surface of the annular body member inside the cavity is defined as the interior surface, and the surface of the annular body member outside the cavity is defined as the exterior surface. The arms define and separate the annular body member into the upper part and the bottom part. The bottom part is positioned beneath the outer bone surface, whereas the upper part is positioned above the outer bone surface. The arms extend radially outward from the annular body member and are positioned above and substantially parallel with the outer bone surface and beneath the soft tissue. The upper part 14 of the percutaneous bone anchored transferring device is thinned to allow deformation if a large load should occur on the percutaneous bone anchored transferring device. This provides a weakened zone. On its inside the percutaneous bone anchored transferring device of this embodiment has a groove 15 for receiving an O-ring 16. In the bottom part 17 of the percutaneous bone anchored transferring device a hole 18 is arranged whereby its outwardly turned limiting surfaces 19 are obliquely arranged. In other words, a limiting surface can be provided within the interior surface of the bottom part by contouring the cavity near its entrance to form an outwardly increasing diameter of the cavity. The bottom part 17 of the percutaneous bone anchored transferring device is suitably textured to allow adaptation to the bone 1 in which it will be introduced. The upper part 14 of the percutaneous bone anchored transferring device is shown as an integrated unit, but can be split into parts connectable by means of a screw joint over the plane in which the arms 12 are arranged. A lip may be provided in the interior surface of the upper part near its entrance to form a ridge for engaging the upset of a lid.

In the transferring part 11 of this embodiment a connection means 21 is introduced from beneath and fixedly arranged to the transferring part 11 by means of a screw joint by means of a locking nut 22. The connection means 21 shows a conical upper limiting surface 23 intended to abut perfectly to the hole 18 and its limiting surfaces 19 of the transferring part 11. In the connection means 21 an electrical connecting unit 24 is arranged the set of cables 6 of which is drawn out through a side opening 25 of the connection means 21.

To the connection means 24 a second connection unit 26 is arranged whereby one unit has male pins or metal sheets and the other unit shows female pins or metal sheets for obtaining a good electrical connection between the connection units 24 and 26. The connection unit 26 is in turn introduced into a middle connection means 31 around which three different poles 32, 33, 34 are arranged and connected via metal sheets or cables to the connection unit 26, which is a unit built by cylindrical parts made of plastic or another non-conducting material. In the center of the middle insert 31 a contact metal sheet of a plus pole 32 is placed. From this plus pole 32 a connecting line leads to a corresponding plus pole 26p on the connection unit 26. Around upper cylindrical part of the middle insert a contact metal sheet of a signal pole 33 is placed and is connected to a corresponding signal pole 26s of the connection unit 26. Further, there is a contact metal sheet of a minus pole 34 arranged around the lower cylindrical part of the middle insert 31, whereby this minus pole 34 is in contact with a corresponding minus pole 26m of the connection unit 26, not shown.

Figure 11:
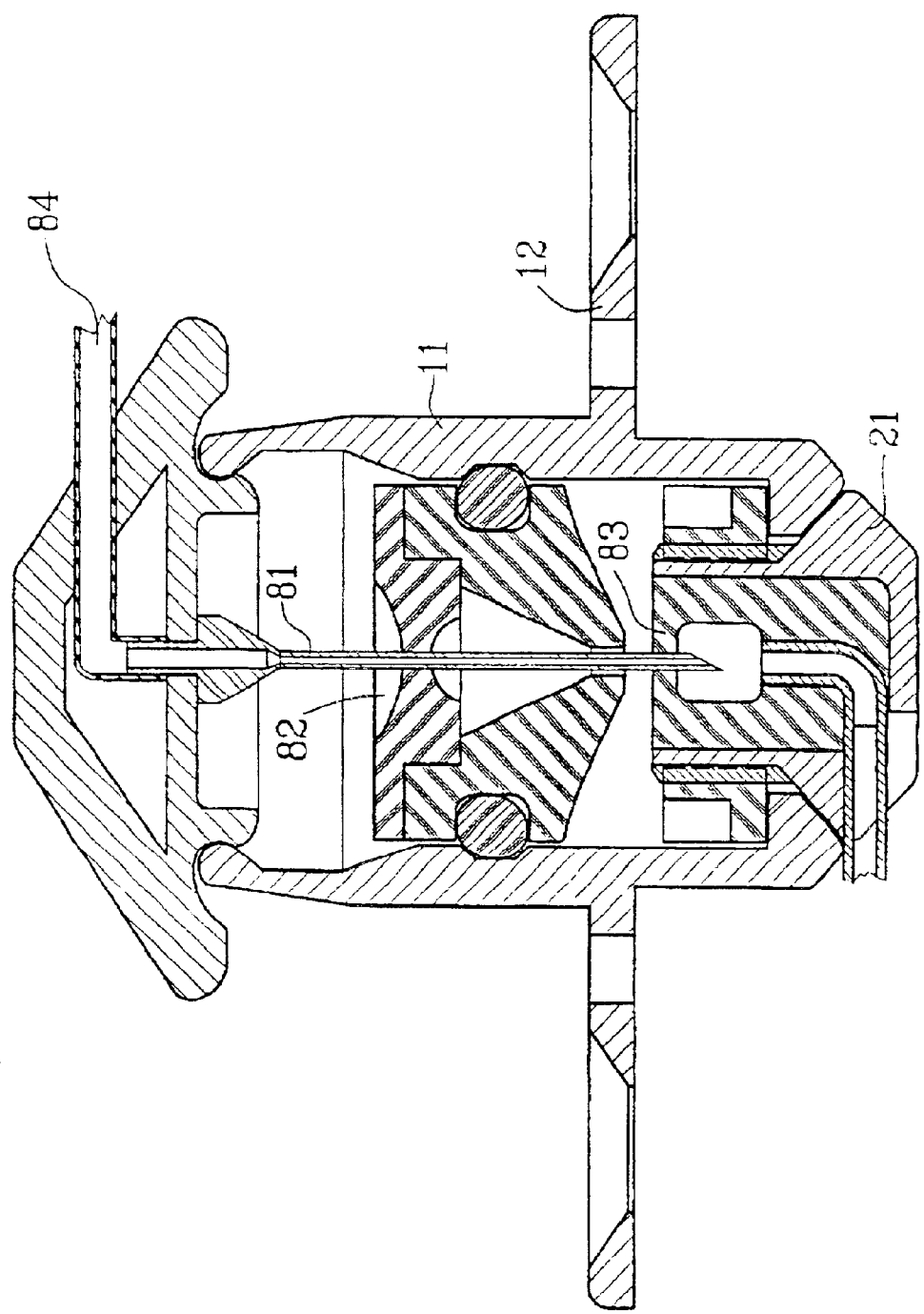
FIG. 11 shows an embodiment of the invention designed to be used for the distribution of a drug and evacuation or airing of internal cavities.

An outer contact 41 is connected to the middle connection means 31, 32, 33, 34 with its different contact metal sheets, which contact can be a microphone unit of a hearing aid, another signal treatment unit, or as evident from FIG. 11, it can be a unit for the distribution of drugs or airing of a cavity. The outer contact 41 comprises a number of pins 42, 43 (not shown), and 44 which connect to their respective contact metal sheet 32, 33, and 34. The pins 42 abut to the center contact metal sheet 32 whereby in the connecting position it is flexed outwardly from the center to rest against the sheet 32. In the same way the point of the sheet 43 pre-bent outwardly to connect to the sheet 33. The pins 44 are pre-bent inwardly towards the center to connect to the edge of the contact sheet 34, which edge can be made stepped to allow stepping/variation of the position of the contact house/hearing apparatus from a rotational point of view. Hereby the sheet 34 is bent in an upward direction on two facing points to allow the pins 44 to be brought down beneath the edge of the contact sheet.

The pins 44 have a primary task to retain the outer contact 41 to the middle connecting means 31. At a load being high enough the pins will, however, pass over the edge to create a security release of the outer contact part from the inner middle insert and thereby the whole transferring device.

Figure 8:
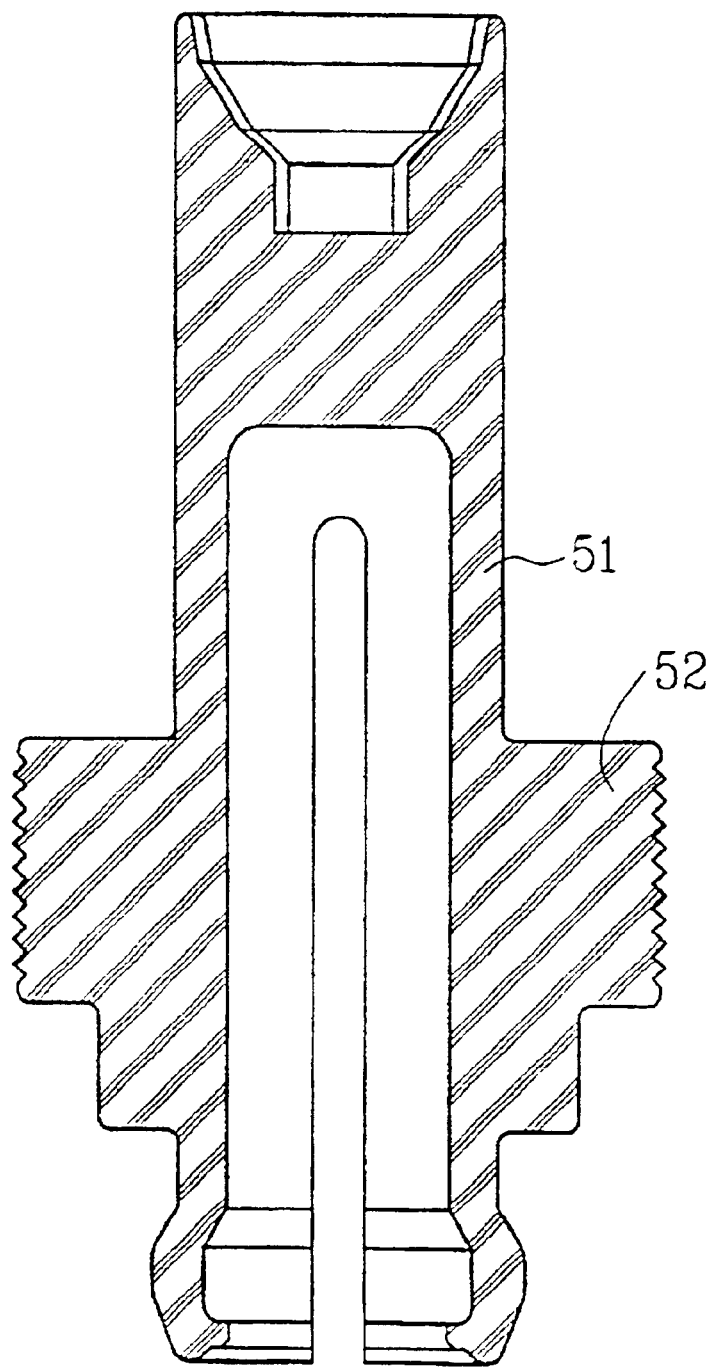
FIG. 8 shows a simple tool for mounting and dismounting the middle connecting unit.

In FIG. 8, 51 denotes a tool for removal and insertion of the middle connection means comprising the connection units from the transferring device 11. The tool 51 is tubular and slotted in such a way that it by means of the grip 52 can be pressed together to retain a middle connection means 31.

Figure 10:
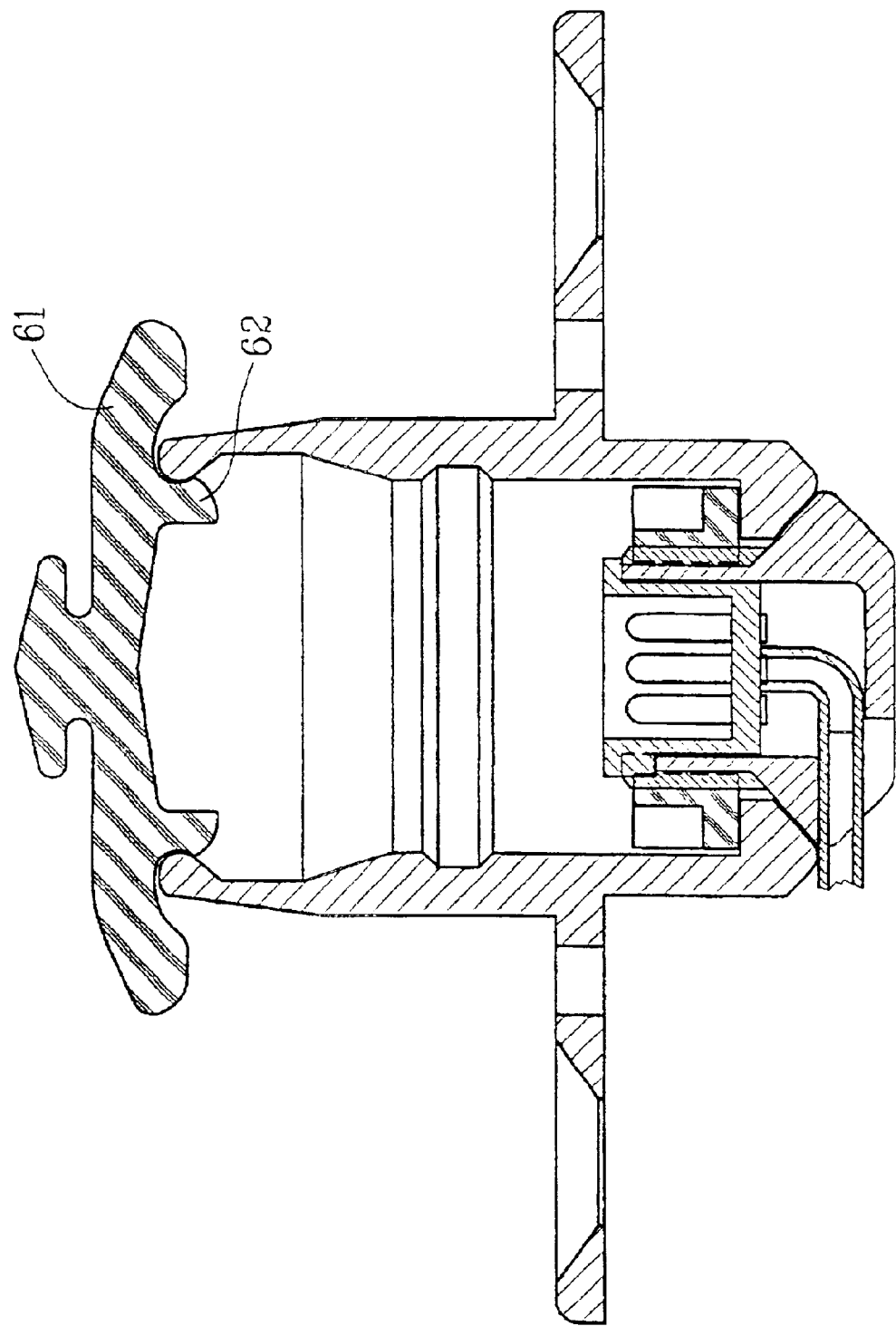
FIG. 10 shows a lid used when the middle connecting unit and its contact surfaces should be protected, for example while taking a bath in salt water, and having a sauna.

In FIG. 10 a lid 61 is shown, which can be placed over the middle insert 31 when the outer contact 41 has been removed. It is suitable to apply the lid 61 when visiting a sauna or being in salt water. In this embodiment the lid 61 contains an upset 62 which snaps down over the upper edge of the transferring device 11.

Figure 9:
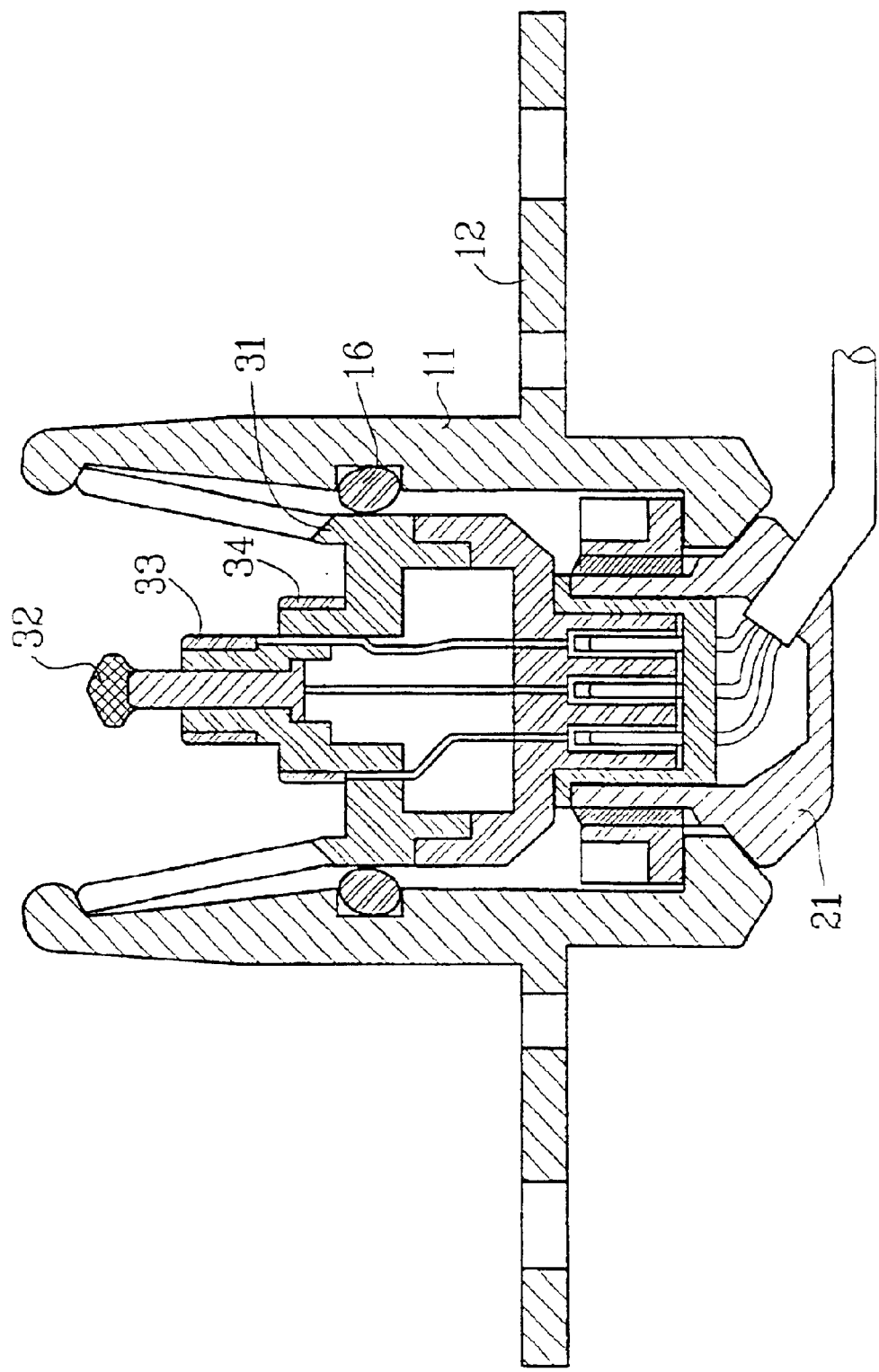
FIG. 9 shows an alternative embodiment of the middle connecting unit, where the middle connecting unit is fixed by means of slotted radially spring biased arms.

In FIG. 9 an alternative means of securing the middle insert 31 is shown, whereby its upper part is slotted and stretches outwardly, whereby this upper part stretches in beneath the edge of the upper part of the transferring device 11, the upper edge of which is upset.

Further, the embodiment shows an alternative arrangement of the O-ring.

Figure 12:
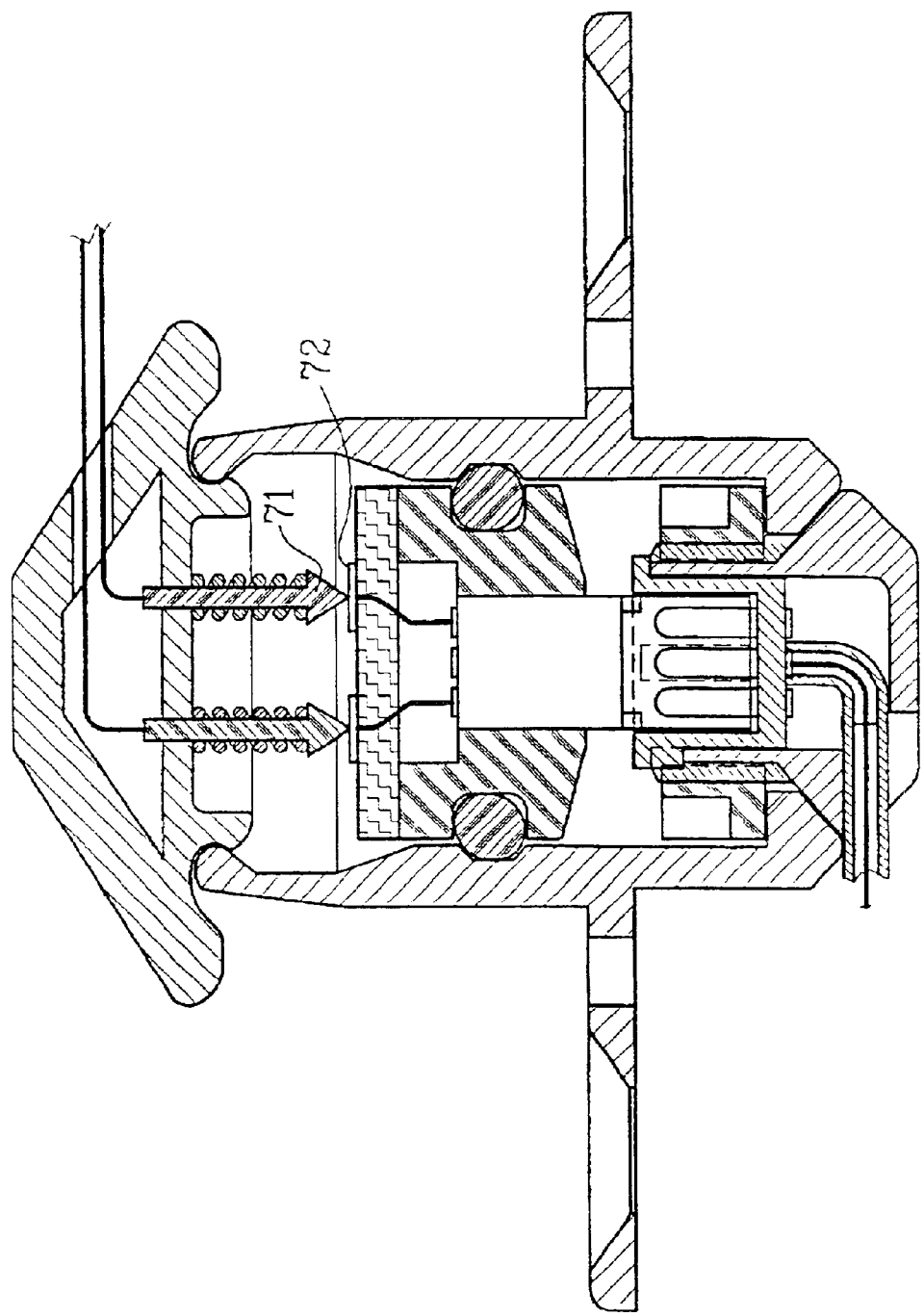
FIG. 12 shows an alternative design of the outer contact unit where the contact metal sheets of the outer contact unit are connected using an axial contact force.

In FIG. 12 an alternative design of the contact means is shown having an axially elastic contact pin 71 which abuts a circuit card 72 provided with circuit lines.

FIG. 11 shows, as mentioned, an embodiment for the distribution of drugs in the form of a solution whereby an injection needle 81 penetrates a membrane 82 arranged in the middle insert as well as a membrane 83 arranged in the connection means. A tube 84 connects to the injection needle 81 for the addition of a drug solution, as well as a tube from the lower part of the connection means for the distribution at a suitable site in the body. These tubes and the injection needle can be used for the airing of a cavity, as well, such as a middle ear suffering from continuous inflammations.

Alternatively, the invention can be described as follows. This invention also provides a connecting device to be used in conjunction with the percutaneous bone-anchored transferring device. The connecting device comprises a first connection unit, a middle connecting unit, and an outer contact unit. The first connection unit comprises: a wall member and a flange. The wall member defines a substantially cylindrical cavity having an open top and a partially-closed bottom. The flange extends outward around a circumference of the wall member. The wall member is shaped to fit at least partially inside the bottom part of the percutaneous bone-anchored transferring device such that the open top is introduced into the cavity of the bottom part of the percutaneous bone-anchored transferring device and the partially-closed bottom abuts the exterior surface of the bottom part of the percutaneous bone-anchored transferring device. The partially-closed bottom contains a side opening.

The middle connecting unit is a substantially cylindrical holder, with a first end and a second end and an opening extending completely through from the first end through the second end, designed to fit inside the cavity of the upper part of the percutaneous bone-anchored transferring device such that the first end is positioned near the first connection unit.

The outer contact unit is a substantially cylindrical holder having a lower end and an upper end, wherein the lower end is designed to fit inside the cavity of the upper part of the percutaneous bone-anchored transferring device such that the lower end is positioned near the second end of the middle connecting unit, and wherein the upper end is designed to reside above the upper part of the percutaneous bone-anchored transferring device.

An alternate design of the flange on the first connection unit has a triangular cross section with the base of the triangular cross section contiguous with the wall member and the apex extending radially outward from the wall member such that the apex is extending its maximum amount near the partially-closed bottom. The purpose of this alternative design is so that when the open top is introduced into the cavity of the bottom part of the percutaneous bone-anchored transferring device, the flange abuts to the limiting surface of the percutaneous bone-anchored transferring device. Another alternate design for the flange is that the bottomward side of the triangle section forms a taper at the bottom of the connecting device.

Additional features may be built into the connecting device. For example, in the first connection unit, the open top of the wall member can be releasably connected to the interior surface of the percutaneous bone-anchored transferring device using a screw joint and locking nut. Also the open top of the wall member can be provided with a membrane. Another example is that the outer contact unit can releasably arranged in the middle connecting unit such that the outer contact unit and the middle connecting unit will be released from each other at a predetermined load on the outer contact unit. Yet another example, is that the middle connecting unit can be provided with a membrane. The middle connecting unit may also contain a circular groove extending all the way around for securing an o-ring. Also, the middle connecting unit may contain slotted radially spring-biased arms that rest against the interior surface of the upper part of the percutaneous bone-anchored transferring device. The middle connecting unit may also comprise a number of electrically conductive contact sheets for obtaining an electrical transfer.

In one particular embodiment of the invention, the following additional components are added: an electrical connection unit, a second connection unit, and three different poles (a positive pole, a negative pole, and a signal pole). The electrical connection unit has an upper surface and a lower surface, wherein the electrical connection unit is arranged inside the first connection unit such that a set of cables extending from the lower surface of the electrical connection unit is drawn out through the side opening of the first connection unit and electrically conductive elements extend from the upper surface of the electrical connection unit. The second connection unit comprises electrically conductive contacts on a first side and a positive pole, a negative pole, and a signal pole on a second side, wherein the electrically conductive contacts on the first side contact the electrically conductive elements of the upper surface of the electrical connection unit such that an electrical connection is formed between the electrical connection unit and the second connection unit. The second connection unit is in turn introduced into first end of the middle connecting unit. The three different poles (a positive pole, a negative pole, and a signal pole) are arranged around the second end of the middle connecting unit and connected to the corresponding poles on the second side of the second connection unit and connected via metal sheets or pins to the outer contact unit.

The invention may also be described as a system comprising a percutaneous bone-anchored transferring device and a connecting device as described above.

The invention also provides a method for percutaneously transferring electrical signals or energy to and/or from an implanted unit or for the administration of a chemical or evacuation or airing of internal cavities using a system comprising a percutaneous bone-anchored transferring device and a connecting device as described above. The method comprises the steps of: (1) placing an implanted unit into a subject through a bore hole that has been made through soft tissue and bone of the subject; (2) connecting the implanted unit through the first connection unit of the connecting device to the middle connecting unit; (3) placing the percutaneous bone-anchored transferring device over the first connection unit and middle connecting unit and into the bore hole such that the bottom part of the percutaneous bone-anchored transferring device is inside the bore hole and the radial arms are resting on the outer surface of the bone with the tissue temporarily moved to a side; (4) fastening the radial arms into the bone; (5) connecting the outer contact unit to the middle connecting unit; (6) connecting the outer contact unit to an outer device; and (7) activating the outer device to transfer electrical signals or energy to and/or from the implanted unit or to administer a chemical through the implanted unit or to evacuate or air internal cavities through the implanted unit.

The invention also provides a method for using a system comprising a percutaneous bone-anchored transferring device and a connecting device as described above. The method comprises the steps of: (1) connecting an implanted unit, which has been placed into a subject through a bore hole made through soft tissue and bone of the subject, through the first connection unit of the connecting device to the middle connecting unit; (2) placing the percutaneous bone-anchored transferring device over the first connection unit and middle connecting unit and into the bore hole such that the bottom part of the percutaneous bone-anchored transferring device is inside the bore hole and the radial arms are resting on the outer surface of the bone with the tissue temporarily moved to a side; (3) fastening the radial arms into the bone; (4) connecting the outer contact unit to the middle connecting unit; and (5) connecting the outer contact unit to an outer device. This method may also comprise the additional steps of: (6) disconnecting the outer contact unit from the middle connecting unit; (7) placing a lid over the upper part of the percutaneous bone-anchored transferring device; and (8) placing the soft tissue over the lid.

What is claimed is:

1. A connecting device to be used in conjunction with a percutaneous bone-anchored transferring device, the percutaneous bone-anchored transferring device having an annular body member manufactured of a tissue-compatible material, the annular body member comprising a cavity, an interior surface, an exterior surface, an upper part and a bottom part, wherein the cavity extends from the upper part to the bottom part, and wherein the surface of the annular body member inside the cavity is defined as the interior surface, and wherein the surface of the annular body member outside of the cavity is defined as the exterior surface, and having radial arms extending radially outward from the annular body member along a line defining the transition between the upper part and the bottom part, wherein the radial arms are manufactured of a tissue-compatible material, and wherein one or more of the radial arms contains at least one hole, said connecting device comprising:

a first connection unit, wherein the first connection unit comprises:
a wall member defining a substantially cylindrical cavity, said cylindrical cavity having an open top and a partially-closed bottom; and
a flange extending outward around a circumference of the wall member,
wherein the wall member is shaped to fit at let partially inside the bottom part of the percutaneous bone-anchored transferring device such that the open top is introduced into the cavity of the bottom part of the percutaneous bone-anchored transferring device and the partially-closed bottom abuts the exterior surface of the bottom part of the percutaneous bone-anchored transferring device, and wherein the partially-closed bottom contains a side opening;

a middle connecting unit, wherein said middle connecting unit is a substantially cylindrical holder, with a first end and a second end and an opening extending completely through from the first end through the second end, designed to fit inside the cavity of the upper part of the percutaneous bone-anchored transferring device such that the first end is positioned near the first connection unit; and an outer contact unit, wherein said outer contact unit is a substantially cylindrical holder having a lower end and an upper end, wherein the lower end is designed to fit inside the cavity of the upper part of the percutaneous bone-anchored transferring device such that the lower end is positioned near the second end of the middle connecting unit, and wherein the upper end is designed to reside above the upper part of the percutaneous bone-anchored transferring device.

2. The connecting device of claim 1, wherein said flange on the first connection unit has a triangular cross section with the base of the triangular cross section contiguous with the wall member and the apex extending radially outward from the wall member such that the apex is extending its maximum amount near the partially-closed bottom, and wherein a limiting surface is provided within the interior surface of the bottom part of the percutaneous bone-anchored transferring device by contouring the cavity near its entrance to form an outwardly increasing diameter of the cavity, such that when the open top is introduced into the cavity of the bottom part of the percutaneous bone-anchored transferring device, the flange abuts to the limiting surface of the percutaneous bone-anchored transferring device.

3. The connecting device of claim 1, wherein the flange is disposed on the wall member such that the bottomward side of the triangle section forms a taper at the bottom of the connecting device.

4. The connecting device of claim 1, wherein in the first connection unit the open top of the wall member is releasably connected to the interior surface of the percutaneous bone-anchored transferring device using a screw joint and locking nut.

5. The connecting device of claim 1, wherein in the first connection unit the open top of the wall member is provided with a membrane.

6. The connecting device of claim 1, wherein the outer contact unit is releasably arranged in the middle connecting unit such that the outer contact unit and the middle connecting unit will be released from each other at a predetermined load on the outer contact unit.

7. The connecting device of claim 1, wherein the opening of the middle connecting unit is provided with a membrane.

8. The connecting device of claim 1, wherein the middle connecting unit contains a circular groove extending all the way around the middle connecting unit.

9. The connecting device of claim 1, wherein the middle connecting unit contains slotted radially spring-biased arms that rest against the interior surface of the upper part of the percutaneous bone-anchored transferring device.

10. The connecting device of claim 1, wherein the middle connecting unit comprises a number of electrically conductive contact sheets for obtaining an electrical transfer.

11. The connecting device of claim 1, further comprising:

an electrical connection unit having an upper surface and a lower surface, wherein the electrical connection unit is arranged inside the first connection unit such that a set of cables extending from the lower surface of the electrical connection unit is drawn out through the side opening of the first connection unit and electrically conductive elements extend from the upper surface of the electrical connection unit;

a second connection unit comprising electrically conductive contacts on a first side and a positive pole, a negative pole, and a signal pole on a second side, wherein the electrically conductive contacts on the first side contact the electrically conductive elements of the upper surface of the electrical connection unit such that an electrical connection is formed between the electrical connection unit and the second connection unit, and wherein the second connection unit is in turn introduced into first end of the middle connecting unit; and three different poles (a positive pole, a negative pole, and a signal pole) arranged around the second end of the middle connecting unit and connected to the corresponding poles on the second side of the second connection unit and connected via metal sheets or pins to the outer contact unit.

12. A combination of a percutaneous bone-anchored transferring device and a connecting device, wherein the percutaneous bone-anchored transferring device comprises:

an annular body member manufactured of a tissue-compatible material, the annular body member comprising
a cavity,
an interior surface,
an exterior surface,
an upper part and a bottom part, wherein the cavity extends from the upper part to the bottom part, and wherein the surface of the annular body member inside the cavity is defined as the interior surface, and wherein the surface of the annular body member outside of the cavity is defined as the exterior surface; and a plurality of separate radial arms extending radially outward from the annular body member along a line defining the transition between the upper part and the bottom part, wherein the radial arms are manufactured of a tissue-compatible material, and wherein one or more of the radial arms contains at least one hole, and the connecting device comprises:

a first connection unit, wherein the first connection unit comprises:

a wall member defining a substantially cylindrical cavity, said cylindrical cavity having an open top and a partially-closed bottom; and a flange extending outward around a circumference of the wall member, wherein the wall member is shaped to fit at least partially inside the bottom part of the percutaneous bone-anchored transferring device such that the open top is introduced into the cavity of the bottom part of the percutaneous bone-anchored transferring device and the partially-closed bottom abuts the exterior surface of the bottom part of the percutaneous bone-anchored transferring device, and wherein the partially-closed bottom contains a side opening;

a middle connecting unit, wherein said middle connecting unit is a substantially cylindrical holder, with a first end and a second end and an opening extending completely through from the first end through the second end, designed to fit inside the cavity of the upper part of the percutaneous bone-anchored transferring device such that the first end is positioned near the first connection unit; and an outer contact unit, wherein said outer contact unit is a substantially cylindrical holder having a lower end and an upper end, wherein the lower end is designed to fit inside the cavity of the upper part of the percutaneous bone-anchored transferring device such that the lower end is positioned near the second end of the middle connecting unit, and wherein the upper end is designed to reside above the upper part of the percutaneous bone-anchored transferring device.

\* \* \* \* \*